United States Patent [19]

van der Loo et al.

[11] 4,412,984

[45] Nov. 1, 1983

[54] FLAVOR POTENTIATED ORAL COMPOSITIONS CONTAINING THAUMATIN OR MONELLIN

[75] Inventors: Henricus E. van der Loo; Charles Wiener, both of Middletown, N.Y.

[73] Assignee: Talres Development (N.A.) N.V., Curacao, Netherlands Antilles

[21] Appl. No.: 300,807

[22] Filed: Sep. 10, 1981

Related U.S. Application Data

[63] Continuation-in-part of Ser. No. 899,113, Apr. 24, 1978, Pat. No. 4,300,576.

[30] Foreign Application Priority Data

Apr. 26, 1977 [GB] United Kingdom .............. 17335/77

[51] Int. Cl.³ .......................... A61K 7/26; A23L 1/22
[52] U.S. Cl. ......................................... 424/58; 424/48; 424/49; 426/3; 426/548; 426/534; 426/650; 426/651
[58] Field of Search .................. 426/534, 548, 3, 650, 426/651; 424/49, 58, 48

[56] References Cited

U.S. PATENT DOCUMENTS

| | | | |
|---|---|---|---|
| 3,695,898 | 10/1972 | Hill et al. | 426/548 X |
| 3,829,588 | 8/1974 | Finucane | 426/548 |
| 3,878,184 | 4/1975 | Dobry | 426/548 X |
| 3,982,023 | 9/1976 | Bahoshy et al. | 426/548 X |
| 4,001,455 | 1/1977 | La Via et al. | 426/548 |
| 4,036,992 | 7/1977 | Bahoshy et al. | 426/548 X |
| 4,045,581 | 8/1977 | Mackay et al. | 426/548 X |
| 4,122,205 | 10/1978 | Burge et al. | 426/548 |
| 4,277,464 | 7/1981 | Reussner et al. | 426/548 X |
| 4,300,576 | 11/1981 | van der Loo et al. | 426/548 X |

FOREIGN PATENT DOCUMENTS 665556 6/1963 Canada ................................ 426/548

*Primary Examiner*—Joseph M. Golian
*Attorney, Agent, or Firm*—Ostrolenk, Faber, Gerb & Soffen

[57] ABSTRACT

A flavored oral composition contains thaumatin or monellin at a flavor potentiating level, which level is below the sweetness threshold of thaumatin or monellin respectively in the composition; a flavoring composition comprises a solution or dispersion of a flavoring agent in a carrier therefor, and also contains thaumatin or monellin at a flavor potentiating level, which level is below the level required to provide sweetness in a substrate when the flavoring composition is added thereto in a flavoring amount; a method of potentiating and extending the flavor of an oral composition comprises adding thereto thaumatin or monellin at a flavor-potentiating level below the sweetness threshold of thaumatin or monellin respectively.

8 Claims, No Drawings

FLAVOR POTENTIATED ORAL COMPOSITIONS CONTAINING THAUMATIN OR MONELLIN

This application is a continuation-in-part of application Ser. No. 899113 filed Apr. 24, 1978 and now U.S. Pat. No. 4,300,576.

This invention relates to the use of naturally occurring protein sweeteners as flavour modifiers or enhancers for oral compositions.

A proteinaceous material obtained from the fruit of *Thaumatococcus daniellii*, known as thaumatin, is a potent sweetener having a sweetness of two or three thousand times that of sucrose. Tasted in the mouth, thaumatin exhibits a distinctive long-lasting sweetness coupled with a lingering aftertaste reminiscent of liquorice. Another protein sweetener, known as monellin, is obtained from the fruit of *Dioscoreophyllum cumminsii*. Monellin is about a half as sweet as thaumatin. Various combinations of thaumatin or monellin with other sweeteners and sweetness-modifiers have been reported.

Most surprisingly, we have now found that thaumatin and monellin can be used in flavoured oral compositions to potentiate the flavour and to extend the flavour life. This effect is obtained using levels of protein below the detectable sweetness threshold so that no sweetness is being provided. Thus, for example, the flavour of a chewing gum, which flavour normally only lasts about 4 to 5 minutes, can be made to last for up to 20 minutes.

According to the present invention, there is provided a method of potentiating and extending the flavour of an oral composition by adding thereto thaumatin or monellin at a level below the sweetness threshold.

There is also provided a flavoured oral composition containing thaumatin or monellin at a level below the sweetness threshold. All flavours used in such compositions are affected, for example peppermint and spearmint and also fruit flavours. Furthermore, a smoothing effect is noticeable.

There is also provided a flavouring composition comprising a solution or dispersion of a flavouring agent in a carrier therefor, and also containing thaumatin or monellin at a flavour-potentiating level, which level is below the level required to provide sweetness in a substrate when the flavouring composition is added thereto in a flavouring amount.

The term "oral composition" used herein is intended to mean a composition of matter which is taken into the mouth and tasted, either to be subsequently ingested or not. Examples of the former category include foodstuffs, beverages, confectionery, medicines and the like. Examples of the latter category include chewing gum, toothpaste, mouth washes, dental hygiene aids such as disclosing tablets, and the like. The term "oral composition" is further intended to include a composition of matter which is the precursor of a composition which is taken into the mouth and tasted. Examples of this category include uncooked or partially pre-cooked foodstuffs which are to be cooked before use; concentrates for dilution to form beverages, foodstuffs or medicines and dried products for rehydration, such as "instant" soups, desserts and beverages.

The sweetness threshold of thaumatin or monellin is difficult to quantify in the abstract since the sweetness and other flavour characteristics of thaumatin and monellin are strongly affected by the nature of the composition, the pH and other factors. Thus, for example, solid particulate materials can adsorb the protein; surfactants can denature it; and substances such as gums can mask the flavouring effect. However, it is a simple matter to determine the sweetness threshold for any particular composition.

In general, we find that the flavour potentiating level is about 10–75% of the sweetness threshold level. We find, however, that the potentiating effect is far less affected by the factors which affect the sweetness. For thaumatin, we have found that for a mouthwash based on aqueous alcohol, a level of about 0.005% by weight is the sweetness threshhold and the protein is an effective flavour potentiator at levels of 0.00005 to 0.0001%, while the toothpaste containing inorganic abrasives and surfactants which affect the protein, and having a pH on the alkaline side, the threshold is as high as 0.1% and the protein is an effective potentiator at levels of from 0.005 to 0.01%. Clear toothpastes containing no abrasive but some polysaccharides have threshold and potentiation levels about an order of 10 lower. For a conventional chewing gum containing polyvinyl acetate and calcium carbonate, the thaumatin sweetness threshold is about 0.05% and the protein is potentiation-effective at levels of 0.01 to 0.03%.

For coffee, with or without milk or cream, and for tea with milk, the threshold is about 0.001% and the potentiation range is typically from 0.0001 to 0.0005%. For tea without milk the respective threshold figure is about 5 times higher because of the tannin present which denatures the protein but the potentiation level is not increased. For a carbonated beverage, such as a clear lemon-flavoured drink, the threshold is about 0.0004% and the potentiation range is about 0.0001 to 0.0003%.

Other flavours which are potentiated and enhanced include fish and meat extracts, for example those used in oriental cookery, curry, ginger, garlic, onion, mustard, peppermint and other mint flavours, chocolate, vanilla, fruit flavours, cinnamon, wintergreen, licorice and aniseed.

For monellin the above figures can be multiplied by a factor of about 2.5.

One of the problems of using a protein sweetener such as thaumatin and monellin in compositions which are heated at some stage in their preparation, either in a cooking process or to pasteurize or sterilize the compositions, is that the sweetening power of the sweetener can be degraded by the heat. This effect is variable and depends on a number of factors, including the pH and the presence of various ions. A surprising feature of the present invention is that, compared with the sweetening effect, the flavour potentiating action is far less affected by the application of heat. This suggests that the two actions are completely distinct, not only in kind but in source, the flavour potentiating action being much less affected by the denaturing effect of the heat on the protein. For this reason, thaumatin and monellin can be used as flavour potentiators in oral compositions which will or may be heated, for example pasteurised drinks, hot beverages, "instant" foods, food mixes and the like.

The present invention is illustrated by the following non-limiting examples.

EXAMPLE 1

Mouthwash

| Glycerol | 10% by weight |
|---|---|
| ethanol | 10% |
| cetyl pyridinium chloride | 0.05% |

| | | |
|---|---|---|
| -continued | | |
| cinnamon and mint flavour | | 0.066% |
| saccharin | | 0.005 to 0.01% |
| thaumatin | | 0.0001% |
| water | to | 100% |

EXAMPLE 2

Chewing gum

| | |
|---|---|
| Polyvinyl acetate | 20 parts by weight |
| butyl phthalylbutylglycolate | 3 |
| polyisobutylene | 3 |
| microcrystalline wax | 2 |
| calcium carbonate | 2 |
| flavourings | 1 |
| saccharin | 0.1 |
| glucose | 10 |
| thaumatin | 0.005-0.01 (= 0.0125-0.025% for monellin) |

EXAMPLE 3

Toothpaste

An opaque toothpaste has the following composition:

| | | |
|---|---|---|
| dicalcium phosphate (abrasive) | | 50% by weight |
| glycerol (humectant) | | 30% |
| gum tragacanth (binder) | | 1% |
| sodium lauryl sulphate | | 1% |
| methyl parahydroxy benzoate | | 0.03% |
| peppermint oil | | 0.04% |
| saccharin | | 0.5% |
| thaumatin | | 0.05% |
| water | to | 100% |

An equivalent to the clear paste of the conventional type (eg. Close-Up) contains only 0.005% thaumatin because it contains less phosphate.

EXAMPLE 4

Carbonated lemon-flavoured beverage

A beverage concentrate has the following composition:

| | | |
|---|---|---|
| thaumatin | | 3 mg |
| sucrose | | 80 g |
| sodium benzoate | | 160 mg |
| citric acid | | 1.7 g |
| lemonade essence | | 0.8 g |
| water | to | 100 ml |

The concentrate is diluted to 1 liter with carbonated water to give an oral composition in the form of a lemonade drink. The drink has a noticeable lemon tang, compared to a conventional drink omitting the thaumatin.

EXAMPLE 5

Coffee

The addition of thaumatin during conventional processing of coffee beans can potentiate the flavour of the final coffee drink and lead to a reduction in the required amount of coffee beans.

Thus, thaumatin can be added to aqueous coffee bean extracts during preparation of coffee powder or granules, the amount being such as will give 1 to 5 ppm of thaumatin in the final drink, i.e. about 100–600 ppm in the spray-dried or freeze-dried coffee solids. The thaumatin is preferably added immediately prior to drying of the extract, but can also be added to a solution of instant coffee which is then redried.

Assessment by taste panels suggests that a drink containing 0.9% coffee solids and 3 ppm thaumatin has a comparable or better taste to a drink containing 1% coffee solids.

EXAMPLE 6

Tea

In a similar manner to Example 5, thaumatin can improve the flavour of tea. Addition of 1 to 100 microgram thaumatin to each ml of a tea infusion results in a smoother flavour with less bitterness or astringency.

EXAMPLE 7

Flavouring Essences

Thaumatin can be incorporated into flavour essence or oils to enhance and prolong their flavour, for example to potentiate the flavour of the essence or oil when added to chewing gum, candy, soft drinks, etc. This potentiation applies especially in peppermint, spearmint, menthol, coffee, chocolate, vanilla, ginger, orange, strawberry, lemon, apple, cinnamon, wintergreen, licorice and aniseed. Thaumatin is dissolved as a concentrate in water then mixed with ethyl or isopropyl alcohol, and mixed with the essence to give 1–10% thaumatin by weight in the essence or oil.

In the above Examples, the amount of thaumatin can be replaced by about 2.5 times the amount of monellin.

We claim:

1. A flavoured oral composition containing thaumatin or monellin at a flavour potentiating level, which level is below the detectable sweetness threshold of thaumatin or monellin respectively in the composition.

2. The composition of claim 1 containing thaumatin or monellin at a level of about 10–75% of the sweetness threshold.

3. The composition of claim 1, containing a flavour selected from the group consisting of citrus fruit flavours, peppermint, spearmint, menthol, tea, coffee, chocolate, vanilla, ginger, strawberry, apple, cinnamon, wintergreen, licorice, aniseed, curry, onion, garlic, mustard, fish extracts and meat extracts.

4. A flavouring composition comprising a solution or dispersion of a flavouring agent in a carrier therefor, and also containing thaumatin or monellin at a flavour potentiating level, which level is below the level required to provide sweetness in a substrate when the flavouring composition is added thereto in a flavouring amount.

5. The composition of claim 4, comprising an aqueous alcoholic solution of a flavouring essence or flavouring oil selected from the group consisting of peppermint, spearmint, menthol, coffee, chocolate, vanilla, ginger, orange, strawberry, lemon, apple, cinnamon, wintergreen and aniseed.

6. The composition of claim 5, containing thaumatin in an amount of 1–10% by weight of flavouring solution.

7. A method of potentiating and extending the detectable flavour of an oral composition by adding thereto thaumatin or monellin at a flavour-potentiating level below the sweetness threshold of thaumatin or monellin respectively in the composition.

8. The method of claim 7, wherein the said level is about 10–75% of the sweetness threshold.

* * * * *